US00PP07845P

United States Patent [19]

Stravers

[11] Patent Number: Plant 7,845

[45] Date of Patent: Mar. 31, 1992

[54] GERBERA PLANT NAMED TERATY

[75] Inventor: Lambertus J. M. Stravers, Kudelstaart, Netherlands

[73] Assignee: Terra Nigra BV, De Kwakel, Netherlands

[21] Appl. No.: 606,301

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner

[57] ABSTRACT

A new and distinct cultivar of Gerbera plant named Teraty, characterized by its semi-double flower form, red-purple ray floret color, and dark red-purple disc florets with a black eye in center.

1 Drawing Sheet

The present invention comprises a new and distinct cultivar of Gerbera, botanically known as *Gerbera jamesonii*, and referred to by the cultivar name Teraty.

Teraty was originated from a hybridization made in a controlled breeding program in De Kwakel, The Netherlands in 1986 under the supervision of the inventor Lambertus J. M. Stravers.

The female parent was 81D139. The male parent was 85.364. The new cultivar was discovered and selected as one flowering plant within the progeny of the stated parentage by the invention on or about January 1987 in a controlled environment in De Kwakel.

The first asexual reproduction of Teraty was accomplished when vegetative cuttings were taken from the initial selection in April 1987 in a controlled environment in De Kwakel, The Netherlands by a technician working under formulations established and supervised by the inventor. The new cultivar is presently being propagated by cuttings and tissue culture. Horticultural examination of selected units initiated in November 1987 has demonstrated that the combination of characteristics as herein disclosed for Teraty are firmly fixed and are retained through successive generations of asexual reproduction.

Teraty has not been observed under all possible environmental conditions. The phenotype may vary significantly with variations in environment such as temperature, light intensity and day length. The following observations, measurements and comparisons describe plants grown in the greenhouses of Terra Nigra BV in De Kwakel, The Netherlands under controlled conditions which closely approximate those generally used in commercial practice.

The following traits have been repeatedly observed and have been determined to be basic characteristics of Teraty, which in combination distinguish this Gerbera as a new and distinct cultivar:

1. Semi-double flower form.
2. Red-purple ray floret color.
3. Contrasting dark red-purple disc florets with a black eye in center.
4. An inner band of florets which surround the disc and are of the same color as the ray florets.

Of the many commercial cultivars known to the present inventor, there is no cultivar sufficiently similar to Teraty so as to provide a meaningful basis for comparison.

The accompanying photographic drawing shows typical inflorescence and foliage characteristics of Teraty, with the colors being as nearly true as possible with illustrations of this type. The photograph comprises a closeup view of the novel flower form and color of the new cultivar.

In the following description, color references are made to The Royal Horticultural Society Colour Chart (RHS). The color values were determined shortly after 12:00 noon on Dec. 11, 1989 under artificial light at De Kwakel, The Netherlands.

Classification:

*Botanical.*—*Gerbera jamesonii* cv Teraty.

*Commercial.*—Gerbera.

Parentage: Seedling from cross of 81D139 and 85.364.

Plant: The plant when fully grown reaches a height of 40 cm.

Leaf Blade:

*Length.*—Medium.

*Width.*—Medium.

*Thickness.*—Medium.

*Blistering (puckering).*—Medium.

*Hairiness on upper side.*—Dense.

*Depth of cuts or incisions on leaf*—Near bottom or base: Deep. Near middle: Medium. Near tip: Shallow.

*Color.*—Upper surface of leaf, medium green; lower surface, light green.

*Glossiness on upper side.*—Medium.

*Angel at top.*—Weakly acute.

*Shape at top.*—Pointed.

*Margin of lobes.*—Sinuate.

*Petiole length.*—Medium.

*Petiole anthocyanin coloration.*—Present, weak in intensity.

Peduncle:

*Length.*—Medium.

*Cross section.*—Round, medium strength and thickness.

*Resistance to bending.*—Medium.

*Hairiness.*—Medium.

*Color.*—Medium green.

*Anthocyanin.*—Present at base, light in intensity, none present at tip.

*Bracts near tip.*—None.

Flower Head:

*Type.*—Semi-double; generally funnel shaped in form.

*Diameter from edge to edge.*—10 cm.

*Involucre.*—Height: Medium. Diameter: Medium. Number of bracts: Average, longitudinal axis on inner rows are reflexing. Anthocyanin: Present on upper bracts. Hairiness: Medium.

*Outer row ray florets.*—Number in outer row: Medium. Length of floret: Medium. Width of floret: Medium. Shape of floret: Narrow, elliptic, longitudinal folding weak. Shape of tip: Pointed, two teeth, shallow in depth. Axis (longitudinal) of florets: Reflexing. Cross section of floret: Concave. Length of free petals: Short. Color distribution on inner side: Uniform. Striation: Absent. Claw spot: Present. Color on top side: 66C. Color on bottom side: 56A.

*Inner row ray florets.*—Diameter: Large. Color: Pink. Longitudinal axis: Straight.

*Disc florets.*—Diameter: Large. Main color of perianth lobes: White for both male and female flowers. Color (mature and immature): Dark purple.

Reproductive parts:

*Stigma.*—Main color, yellow.

*Anthers.*—Main color: Dark yellow; color at top lighter relative to other part. Longitudinal stripping: Absent.

*Pappus.*—Main color: Yellow; uniform color throughout. Orientation: Level of top is above closed disc florets.

I claim:

1. A new and distinct cultivar of Gerbera plant named Teraty, as illustrated and described.

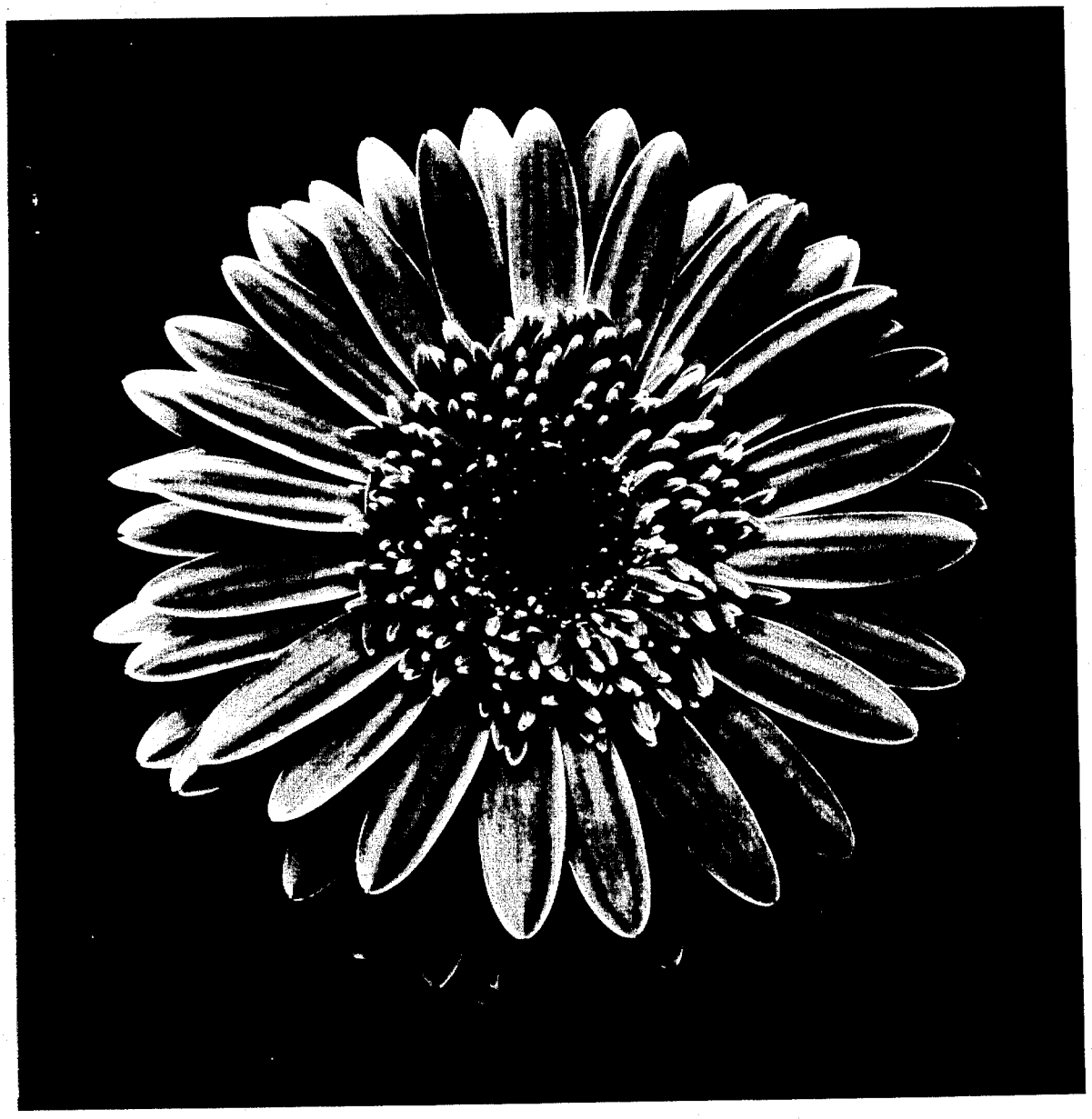

* * * * *